US006217852B1

(12) United States Patent
Gildenberg et al.

(10) Patent No.: US 6,217,852 B1
(45) Date of Patent: Apr. 17, 2001

(54) PERSONAL CLEANSING COMPOSITIONS HAVING PHOTOPROTECTIVE AGENTS

(75) Inventors: Stuart R. Gildenberg, West Bloomfield; Michael T. Siegel, Orchard Lake, both of MI (US); Christopher G. Salentine, San Rafael, CA (US); Manzer J. Durrani, Hudson, OH (US); Debra A. Dow, Petaluma, CA (US)

(73) Assignee: Skinnovative Dermatologic Concepts, L.L.C., Waterford, MI (US)

( * ) Notice: Subject to any disclaimer, the term of this patent is extended or adjusted under 35 U.S.C. 154(b) by 0 days.

(21) Appl. No.: 09/134,882

(22) Filed: Aug. 15, 1998

(51) Int. Cl.$^7$ .............................. A61K 7/42; A61K 7/44; A61K 7/06; A61K 7/00; A61K 7/50

(52) U.S. Cl. ............................. 424/59; 424/60; 424/70.9; 424/401; 510/130; 514/844; 514/846; 514/937; 514/947

(58) Field of Search .............................. 424/401, 59, 60, 424/70.9; 514/844, 846, 937, 947; 510/130

(56) References Cited

U.S. PATENT DOCUMENTS

| | | |
|---|---|---|
| 4,714,609 | 12/1987 | Carden . |
| 4,767,463 | 8/1988 | Brode et al. . |
| 4,837,005 | 6/1989 | Brode, II et al. . |
| 4,847,069 | 7/1989 | Bissett et al. . |
| 4,847,071 | 7/1989 | Bissett et al. . |
| 4,847,072 | 7/1989 | Bissett et al. . |
| 4,857,307 | 8/1989 | Suss et al. . |
| 4,869,897 | 9/1989 | Chatterjee et al. . |
| 4,873,293 | 10/1989 | Brode, II et al. . |
| 4,913,743 | 4/1990 | Brode et al. . |
| 4,946,671 | 8/1990 | Bissett et al. . |
| 4,954,332 | 9/1990 | Bissett et al. . |
| 4,970,216 | 11/1990 | Deckner et al. . |
| 5,011,681 | 4/1991 | Ciotti et al. . |
| 5,028,417 | 7/1991 | Bhat et al. . |
| 5,039,513 | 8/1991 | Chatterjee et al. . |
| 5,084,270 | 1/1992 | Ciaudelli . |
| 5,138,043 | 8/1992 | Polovsky et al. . |
| 5,153,174 | 10/1992 | Band et al. . |
| 5,192,462 | 3/1993 | Gloor et al. . |
| 5,207,998 | 5/1993 | Robinson et al. . |
| 5,209,923 | 5/1993 | Nichols . |
| 5,215,749 | * 6/1993 | Nicoll et al. .......................... 424/401 |
| 5,244,665 | * 9/1993 | Natraj et al. .......................... 424/401 |
| 5,384,115 | 1/1995 | Bissett et al. . |
| 5,384,334 | 1/1995 | Polovsky et al. . |
| 5,439,682 | 8/1995 | Wivell et al. . |
| 5,439,935 | 8/1995 | Rawlings et al. . |
| 5,439,954 | 8/1995 | Bush . |
| 5,456,904 | 10/1995 | Bush . |
| 5,462,963 | 10/1995 | Bush et al. . |
| 5,476,660 | 12/1995 | Somasundaran et al. . |
| 5,486,352 | 1/1996 | Guerrero . |
| 5,487,884 | 1/1996 | Bissett et al. . |
| 5,492,690 | 2/1996 | Bush . |
| 5,505,935 | 4/1996 | Guerrero et al. . |
| 5,534,265 | 7/1996 | Fowler et al. . |
| 5,540,853 | 7/1996 | Trinh et al. . |
| 5,560,918 | 10/1996 | Wivell et al. . |
| 5,576,027 | 11/1996 | Friedman et al. . |
| 5,585,104 | 12/1996 | Ha et al. . |
| 5,599,549 | 2/1997 | Wivell et al. . |
| 5,618,850 | * 4/1997 | Coury et al. ...................... 514/772.2 |
| 5,658,577 | 8/1997 | Fowler et al. . |
| 5,686,084 | 11/1997 | Wenke et al. . |
| 5,702,712 | 12/1997 | Wenke et al. . |
| 5,705,147 | 1/1998 | Shapiro et al. . |
| 5,720,961 | 2/1998 | Fowler et al. . |
| 5,849,310 | * 12/1998 | Trinh et al. .......................... 424/401 |

OTHER PUBLICATIONS

Madhu A. Pathak, "Photoprotection Against Harmful Effects of Solar UVB and UVA Radiation: An Update," Cosmetic Science and Technology Series, vol. 15, Sunscreens: Development, Evaluation, and Regulatory Aspects, Second Edition, Revised and Expanded, edited by Nicholas J. Lowe et al., pp. 59–69, Mar. 1998.

Michael W. Anderson et al., "Broad–Spectrum Physical Sunscreens: Titanium Dioxide and Zinc Oxide," pp. 353–397, Apr. 1998.

Nadim A. Shaath, "Evolution of Modern Sunscreen Chemicals", pp. 3–31, Mar. 1998.

Dr. Robert Bissonnette, "Update on Sunscreens", from Skin Therapy Letter, vol. 2, No. 5, Aug. 11, 1998, 6 pages (http://www.derm.ubc.ca/skintherapy/stl0205.html).

David W. Osborne et al., "Skin Penetration Enhancers Cited in the Technical Literature", Research and Development, Viro Tex Corporation, Texas, Jul. 29, 1998, 27 pages (http://www.pharmtech.com/technica/osborne/osborne.htm).

Formulations, Apr. 6, 1998, 2 pages (http://www.sunsmart.com/formulations.html).

Robin Marks, "The Use of Suncreens in the Prevention of Skin Cancer", from Menzies Foundation Conference, "The Health Consequences of Ozone Depletion", Sep. 9–11, 1996, Hobart, Australia, 9 pages (http://home.vicnet.net.au/~menzies/marks.htm).

"Early Prevention is Key", article from *Dermatology World* (official publication of the American Academy of Dermatology), Mar. 1998 edition, 2 pages.

Formulation 6426/7, Apr. 6, 1998, 1 page (http://www.sunsmart.com/6426–7.html).

(List continued on next page.)

Primary Examiner—Shelley A. Dodson
Assistant Examiner—Marina Lamm
(74) Attorney, Agent, or Firm—Harness, Dickey & Pierce, P.L.C.

(57) ABSTRACT

A composition for use as a sunscreen applied during washing includes photoprotective agents of the organic type (e.g., octylmethoxy cinnamate and oxybenzone), the inorganic type (e.g., titanium dioxide and zinc oxide), or combinations of the organic and inorganic agents. Additional components include skin penetration enhancers, emollients and surfactants. Additional sunscreen combinations include a sunscreen cleanser based upon triethanolamine (TEA).

36 Claims, 2 Drawing Sheets

OTHER PUBLICATIONS

Information on Finsolv TN, APr. 6, 1998, 1 page (http://www.skypoint.com/members/mhevey/1056.html).

About sunSmart Inc., Apr. 6, 1998, 1 page (http://www.sunsmart.com/about_ss.html).

Z–CoteHP1 Technical Data Sheet, Apr. 6, 1998, 1 page (http://www.sunsmart.com/hp1_specs.html).

Z–Cote Technical Data Sheet,Apr. 6, 1998, 1 page (http://www.sunsmart.com/z–cote_specs.html).

Formulations, Apr. 6, 1998, 2 pages (http://www.sunsmart.com/formulations.html).

Happi Features Aug. 1996 Formulary, Apr. 6, 1998, 5 pages (http://www.happi.com/special/general/formaug.htm).

Retin–A fact sheet, Apr. 20, 1998, 1 page (http://www.vitalize.com/cq–rtna.html).

Retin–A/Tretinoin information from regrowth! The Ultimate Online Reference for Hair Loss, Apr. 20, 1998, 2 pages (http://www.regrowth.com/reference/treatments/medicinal/retina.htm).

*SkinCeuticals* Sun Protection information, Apr. 6, 1998, 1 page (http://www.skinceuticals.com/SunProtection.htm).

"Seeking new methods to eclipse the sun", from *Suncare*, Oct. 1997, 5 pages (http://www.dotfinechem.com/manchem/sections/manfeat/sun/).

MSDS for Z–Cote HP1, Apr. 6, 1998, 3 pages (http://www.sunsmart.com/hp1_msds.html).

sunSmart Inc. home page, Apr. 6, 1998, 1 page (http://www.sunsmart.com/list.htm).

*SkinCeuticals* Sun Protection Science, Apr. 6, 1998, 8 pages (http://www.skinceuticals.com/Protection.htm).

Clare Smith, "Re: skin care and slimming formulation", Jul. 24, 1997, 2 pages (http://www.campo–research.com/campo/discuss/messages/10.html).

Jan. 1997 Formulary, Apr. 6, 1998, 2 pages (http://www.happi.com/special/general/formjan.htm).

Dr. M. Balasubramaniam, "Re: skin care and slimming formulation", Aug. 7, 1997, 2 pages (http:///www.campo–research.com/campo/discuss/messages/15.html).

Sun Protection Explained, Apr. 6, 1998, 4 pages (http://www.sunsmart.com/protect.html).

Sun Caps Encapsulated Organic Sunscreens information, Apr. 6, 1998, 2 pages (http://www.sunsmart.com/suncap_broch.html).

Z–Cote HP1 (Hydrophobic Micronfine Zinc Oxide), Apr. 6, 1998, 2 pages (http://www.sunsmart.com/hp1_broch.html).

Jul. 1997 Formulary from HAppi Features, 10 pages (http://www.happi.com/formjul.htm).

List of emollient oils and innovative formula for a sunscreen soap for testing, Dow Pharmaceutical Sciences, Apr. 10, 1998, 2 pages.

Jul. 1996 Formulary from Happi Features, 5 pages (http://www.happi.com/special/general/formjul.htm).

Spectroderm® information, Jun. 4, 1998, 2 pages (http://www.draxis.com/Divisions/dermweb.htm).

Cetaphil® information, Jun. 4, 1998, 1 page (http:/www.cetaphil.com/cleanser).

Velsan® brochure, Clariant Corporation, distributed by D–D Chemco, Inc., 1995, 12 pages.

W.A. Ritschel et al., "Development of an Intracutaneous Depot for Drugs Binding, Drug Accumulation and Retention Studies, and Mechanism of Depot", *Skin Pharmacology*, vol. 4, 1991, pp. 235–245.

J. Rojas et al., "Optimization of binary and ternary solvent systems in the percutaneous absorption of morphine base", *STP Pharma Sciences*, No. 1, Jan.–Feb. 1991, pp. 70–75.

Adam C. Watkinson et al., "Aspects of the transfermal delivery of prostaglandin", *International Journal of Pharmeceutics*, vol. 74, 1991, pp. 229–236.

R. Panchagnula et al., "Development and Evaluation of an Intracutaneous Depot Formulation of Corticosteroids Using Transcutol as a Cosolvent: In–vitro, Ex–vivo and In–vivo rat Studies", *Journal Pharm. Pharmacol.*, vol. 43, 1991, pates 609–614.

C.M. Chiang et al., "Enhancement of Skin Permeation of Estrogen and Progestogens Through Human Cadaver Skin from Binary Vehicles", Cygnus Research Corporation, Redwood City, California, from AAPS National Annual Meeting, Las Vegas, Nevada, Sep. 1990, 1 page.

F.Reig–Falson et al., "Characterization of the Enhancing Effect of a Vehicle in a Transdermal System", from the 8th Pharmaceutical Technology Conference, vol. I, Monte Carlo, 1989, 15 pages.

Chia–Ming Chiang, Ph.D., "Effects of Enhancers on Transdermal Delivery", presented at the 27th Journess Galeniques de Saint–Remy de Provence, May 1993, 31 pages.

Julian E. Harrison et al., "The Relative Effect of Azone® and Transcutol® on Permeant Diffusivity and Solubility in Human Stratum Corneum", *Pharmaceutical Research*, vol. 13, No. 4, 1996, pp. 542–546.

Francoise Falson–Rieg, "Taking Advantage of the Excipient–Skin Partnership to Modify Percutaneous Absorption", *B.T. Gattefossé*, No. 84, 1991, pp. 17–25.

F. Rieg–Falson, "Optimisation of Percutaneous Absorption of Morphine and Morphine Hydrochloride from Binary Solvent Systems", *B.T. Gattefossé*, No. 81, 1988, pp. 69–77.

M. Yazdanian et al., "The Effect of Diethylene Glycol Moneothyl Ether as a Vehicle for Topical Delivery of Ivermectin", *Veterinary Research Communications*, No. 19, 1995, pp. 309–319.

Leo Pavliv et al., "Topical formulation development of a novel thymidylate synthase inhibitor for the treatment of psoriasis", *International Journal of Pharmaceutics*, No. 105, 1994, pp. 227–233.

David W. Osborne et al., "Skin Penetration Enhancers Cited in the Technical Literature", Jun. 4, 1998, 27 pages (http://www.pharmtech.com/technical/osborne/osborne.htm).

Elinor Chen et al., "Transcutol Effect on Topical Delivery of Ivermectin", *AAPS*, 1992, 1 page.

Pathak, "Photoprotection Against the Harmful Effects of UVA and UVB Radiation", *Photoprotection: An Update*, pp. 71–79, Mar. 1998.

Murphy, "FDA Review of OTC Drug Sunscreen Products", *Regulatory Aspects: United States*, pp. 202–260, Mar. 1998.

* cited by examiner

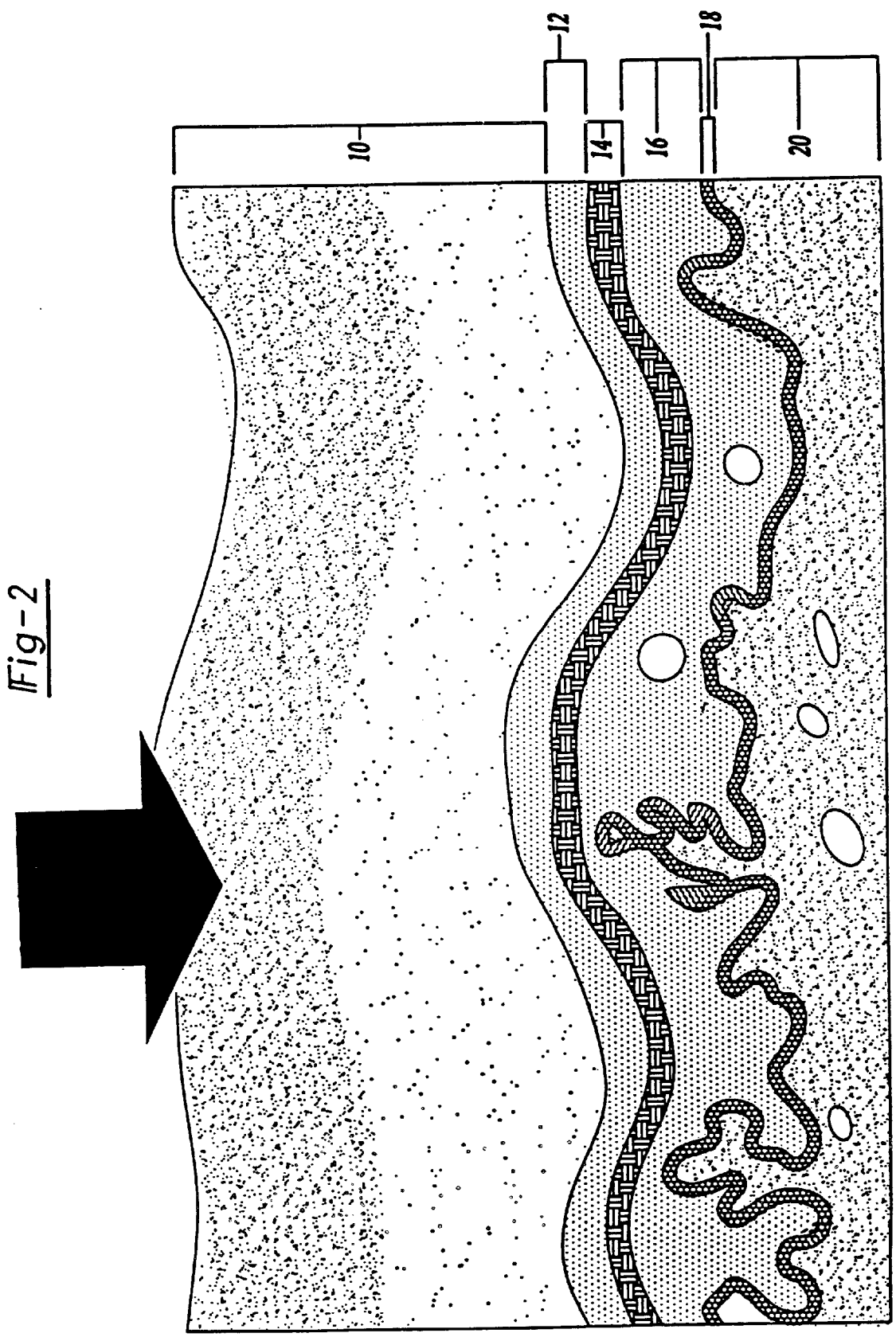

PERSONAL CLEANSING COMPOSITIONS HAVING PHOTOPROTECTIVE AGENTS

BACKGROUND OF THE INVENTION

1. Technical Field

The present invention relates to a sunscreen that is topically applied using a cleanser. More particularly, the present invention relates to personal cleansing compositions having photoprotective agents which consist of chemical sunscreens, physical sunscreens, or both in combination, one or more cleansing agents, and a vehicle for enhancing absorption into the wearer's skin.

2. Discussion

Modern science has become acutely aware of the effects of the sun on human skin, particularly in the latter part of the twentieth century. Of particular concern is that form of solar radiation which occupies the range between 290 and 400 nm, ultraviolet radiation. Overexposure of the human skin to ultraviolet radiation has many deleterious results. One such result of acute overexposure is sunburn, which is felt to be a risk factor in the development of melanoma skin cancer. Serious results of chronic overexposure include premature aging (photoaging) of the skin, the development of precancerous growths (actinic keratoses) and the development of nonmelanoma skin cancers such as basal cell or squamous cell skin cancers.

Two sub-bands of ultraviolet radiation which penetrate the atmosphere are generally known. The first is ultraviolet A (UVA) in the 320 to 400 nm band, and the second is ultraviolet B (UVB) in the 290–320 nm band. (There is also ultraviolet C, but this radiation is absorbed by the earth's atmosphere and does not reach the earth's surface.) Ultraviolet A represents a wider nm scope and is more penetrative in the skin (160–250 $\mu$m) than is ultraviolet B (17–49 $\mu$m). However, it is ultraviolet B which is believed to pose the greatest threat to the human skin in terms of sunburn, aging, and skin cancers. Regardless, ultraviolet radiation of all types can cause the generation of damaging free radicals. These molecular fragments are highly reactive and are known to degrade human tissue by causing destruction at both cellular and molecular levels.

Modern lifestyle has contributed to skin damage due to increased exposure to ultraviolet radiation. It is believed that there are at least two reasons for the heightening of the problem. First, while the early part of the present century taught that fairness of skin, as an attribute of the privileged class, was a desirable feature causing people to avoid exposure to the sun, attitudes changed by the 1920's such that a "healthy tan" began to be regarded as a desirable feature. Suntanning became a popular pastime, and bathers began to seek out sunny climes. Outdoor activities such as golf, camping, tennis, and swimming also captured increased interest in the 1950's.

As a practical matter, ultraviolet exposure occurs during all daylight hours, and includes both reflected and direct light. In reality, the majority of sun exposure during one's lifetime most probably occurs when people are not paying attention—at school or work, on a playground, out shopping, while talking to a neighbor out-of-doors, even while driving a car. The fact is that we are exposed to ultraviolet light from almost every direction every daylight hour. (The inventors regard this as "insensible" exposure.)

A second possible reason for the increase of damage due to ultraviolet radiation is due to the increase of ozone layer-destroying atmospheric pollutants primarily in the forms of chlorofluorocarbons and halogens. The negative impact on the ozone layer by these chemicals has led to increased amounts of ultraviolet radiation actually reaching the earth's surface and, coincidentally, the human population.

Efforts to counteract the damage effected by ultraviolet radiation have primarily included (1) avoidance of sunlight, particularly during certain times of day (particularly peak sunlight hours), (2) the wearing of appropriate clothing to physically block the sun, and (3) topically-applied sunscreen lotions, gels, creams, and sprays. Sometimes the first approach is impossible, particularly during the summer months when many activities are held out-of-doors. The second approach is probably underutilized, but in any event is not always practical.

The third approach—topically applied compounds—have demonstrated varying degrees of effectiveness. These compounds are readily available yet are underutilized for a variety of reasons, including inconvenience and feel. The consumer may select from a host of different products available in the marketplace. Selections are typically made based upon the sun protective factor (SPF) rating of the product, the SPF value providing a guide as to the effective UVB protection the particular selection would offer. Selections can also offer "broad spectrum" coverage which would include protection from UVA radiation as well. A standardized method for quantifying UVA protection is not currently in use.

Topical sunscreen products have SPF values in a wide range, with values typically between 2 and 60. "SPF" is defined as the ratio of the time of UVB exposure necessary to produce minimally detectable erythema in sunscreen-protected skin to that time for unprotected skin. The SPF is inversely proportional to the amount of UVB which passes through to the cutaneous surface. A product having an SPF value of 2 reduces ultraviolet B radiation exposure to the skin by 50% by allowing ½ of UVB to penetrate, while a product having an SPF value of 4 presents a reduction of 75% by allowing ¼ or 25% of UVB to penetrate. An SPF value of 15 demonstrates a reduction of ultraviolet B exposure by over 90%, while exposure is reduced in excess of 98% when the SPF value is 60.

These numbers, however, may be misleading. It is believed by many that only those products having SPF values of 15 or over are of value to the wearer. While it is true that higher SPF factors offer significant protection when used, such products are usually applied only in anticipation of intense sun exposure. It is, in fact, the total sunlight exposure over the person's lifetime which determines the risk of photodamage and most skin cancers. It may not be intense sun exposure during recreational activity which contributes greatest to this lifetime exposure, but daily, constant, intermittent, insensible exposure to the sun that contributes most significantly to the lifetime accumulation of photodamage. Accordingly, the consistent use on a daily basis of lower SPF sunscreens could result in a decrease in the lifetime UVB radiation exposure compared to the inconsistent use of higher SPF photoprotectants. This is especially true once again in that sunscreens are most often used only on days of anticipated high-level exposure and usually not at all on most days.

In addition, consistent daily sunscreen use may delay the onset of skin cancers. It is felt that many years often intervene between sun exposure and skin cancer onset. It is thus proposed that the constant use of sunscreen of SPF 16 could theoretically delay the onset of squamous cell carcinoma until the age of 600 years. Along these lines, one need only regularly apply (through daily application) a product having an SPF value of 4 throughout one's life to prevent the onset of squamous cell skin cancer due to ultraviolet radiation until well beyond the normal life span. (Marks, *The Use of Sunscreens in the Prevention of Skin Cancer*, presented to the Menzies Foundation Conference, Hobert, Australia, Sep. 9–11, 1996.)

It is important to note that sunscreens of any type are not recommended as the primary source of protection from ultraviolet radiation, but as an adjunct to proper skin protection offered by clothing and through measures directed to the avoidance of unnecessary exposure.

The action of a topical sunscreen product is generally based upon one of two mechanisms: Chemical absorption or physical blocking. Chemical sunscreens typically include one or more ultraviolet-absorbing chemical components, such as a benzophenone, a salicylate, or a cinnamate provided in various levels of concentration. While generally effective at absorbing ultraviolet B radiation, these products may fail to effectively protect against ultraviolet A radiation. These products have also been reported to occasionally cause a reaction to the wearer.

As an alternative to the chemical sunscreen, so-called physical or inorganic sunscreens are known. These products utilize particles of zinc oxide or titanium dioxide suspended in a carrier for topical application and physically scatter, reflect, and absorb ultraviolet radiation. The inorganic sunscreens provide effective protection against both ultraviolet B and ultraviolet A radiation. However, because of their white appearance (titanium dioxide is used a white pigment in paints, rubber and plastics), these sunscreens have the significant drawback of leaving the wearer appearing to have been painted white. By micronizing the zinc oxide and titanium dioxide particles, it is possible to eliminate the ordinary white coating and provide a substantially clear coat.

Regardless of form, the known topical sunscreens share a common undesirable characteristic—inconvenience. Topical sunscreens, whether chemical- or physical-based, are time-consuming to apply, and tend to be oily and uncomfortable to wear. Despite increasing public awareness of the value of daily photoprotection, the fact is that over 70% of Americans do not apply sunscreens, hence most people still face the ravages of daily exposure to ultraviolet radiation without protection. (U.S.A. Weekend, Mar. 6–8, 1998, under caption "A Nation That Takes Health Risks.")

Aware of this drawback, efforts have been made in the past to vary the method of applying a sunscreen to the wearer. Examples of the variety of these approaches are presented in: U.S. Pat. No. 5,547,659, issued on Aug. 20, 1996, for PHOTOPROTECTION COMPOSITIONS; U.S. Pat. No. 5,545,399, issued on Aug. 13, 1996, for COSMETIC COMPOSITION; U.S. Pat. No. 5,518,712, issued on May 21, 1996, for WATER RESISTANT SUNSCREEN PROTECTION AND INSECT REPELLANT; U.S. Pat. No. 5,505,935, issued on Apr. 9, 1996, for SUNSCREEN COMPOSITIONS; U.S. Pat. No. 5,487,884, issued on Jan. 30, 1996, for PHOTOPROTECTION COMPOSITIONS COMPRISING CHELATING AGENTS; U.S. Pat. No. 5,486,352, issued on Jan. 23, 1996, for SUNSCREEN COMPOSITIONS; U.S. Pat. No. 5,456,904, issued on Oct. 10, 1995, for PHOTOPROTECTION COMPOSITIONS COMPRISING CERTAIN CHELATING AGENTS; U.S. Pat. No. 5,384,115, issued on Jan. 24, 1995, for PHOTOPROTECTION COMPOSITIONS COMPRISING A RADICAL SCAVENGING COMPOUND AND AN ANTI-INFLAMMATORY AGENT; U.S. Pat. No. 5,306,485, issued on Apr. 26, 1994, for SUNCARE COMPOSITIONS; U.S. Pat. No. 5,244,665, issued on Sep. 14, 1993, for COSMETIC COMPOSITION; U.S. Pat. No. 5,219,558, issued on Jun. 15, 1993, for PHOTOPROTECTION COMPOSITIONS HAVING IMPROVED SUBSTANTIVITY; U.S. Pat. No. 5,215,749, issued on Jun. 1, 1993, for COSMETIC COMPOSITION; U.S. Pat. No. 5,208,011, issued May 4, 1993, for ULTRAVIOLET RESISTANT SUNSCREEN COMPOSITION; U.S. Pat. No. 5,207,998, issued on May 4, 1993, for SUNCARE COMPOSITIONS; U.S. Pat. No. 5,196,187, issued on Mar. 23, 1993, for COSMETIC COMPOSITION; U.S. Pat. No. 5,188,831, issued on Feb. 23, 1993, for SUNSCREENS CONTAINING BOTH WATER AND OIL DISPERSIBLE TITANIUM DIOXIDE PARTICLES; and U.S. Pat. No. 5,028,417, issued Jul. 2, 1991, for SUNSCREEN COMPOSITIONS, all incorporated by reference herein.

While representing improvements in the art of sunscreen application, these references fail to provide an effective sunscreen-soap combination which demonstrates appreciable efficacy, longevity, or substantivity.

SUMMARY OF THE INVENTION

It is an object of the present invention to provide a personal cleansing composition having photoprotective agents which overcome the difficulties associated with the prior art.

More particularly, it is an object of the present invention to provide a personal cleansing composition which may be readily applied.

It is a further object of the present invention to provide such a composition which may be applied coincidentally while the wearer is washing.

Still a further object of the present invention is to provide such a composition which may include an organic sunscreen, an inorganic sunscreen, or a combination of the two.

A further object of the present invention is to provide broad spectrum coverage UVA as well as UVB protection.

Yet an additional object of the present invention is to selectively provide enhancers to improve penetration of at least a portion of the composition into the wearer's skin so as to improve efficacy (i.e., the SPF) and longevity (i.e, the duration of action) of the sunscreen.

Still a further object of the present invention is to provide a composition which demonstrates improved substantivity, whereby the degree of protection is maintained for at least eight hours following application of the composition through washing.

A further object of the present invention is to selectively provide enhancers to improve penetration of at least a portion of the composition into the wearer's skin so as to provide a means to reduce the production of free radicals.

These and other objects of the present invention are achieved by the provision of a personal cleansing composition having photoprotective agents.

The photoprotective agents of the present invention include those of the organic type (e.g., octylmethoxy cinnamate and oxybenzone), the inorganic type (e.g., titanium dioxide and zinc oxide), or combinations of the organic and inorganic agents. Preferably, but not exclusively, the physical type of photoprotection agent would be provided in micronized form. Additional components include skin penetration enhancers, emollients and surfactants, all provided in safe and effective amounts. Additional sunscreen combinations are also set forth, including a sunscreen soap based upon triethanolamine (TEA; a mixture of monoethanolamine, diethanolamine, and triethanolamine used as an emulsifying agent and as a skin penetration enhancer). Further variations include the use of chemical types of photoprotective agents provided in a matrix.

In addition, soapless cleansers (e.g., Oilatum® AD [trademark, Stiefel Laboratories], Aquanil™ [trademark, Person & Covey, Inc.], Cetaphil® [trademark, Galderma Laboratories, Inc.] or SpectroDerm® [trademark, Draxis Pharmaceutical Inc.]) may be usable as the cleansing component of the present invention.

The cleansing vehicle is a soap and may be of the liquid ("soft-soap"), bar, gel, foam or powder varieties. Such varieties may include cleansing lotions or cleansing creams. It is also conceivable that the cleansing vehicle may be a spray as well.

The composition of the present invention finds particular application as an adjunct to the regimen of minimizing exposure to the sun through use of skin-covering clothing as well as using topical sunscreens when prolonged exposure to the sun is anticipated. (See, in addition, *The Use of Sunscreens in the Prevention of Skin Cancer*, supra, pages 4–5.)

The present invention demonstrates superior longevity such that there is not a significant diminution of SPF value.

In general, experimental results have demonstrated sunscreen compositions according to the present invention having SPF values of generally between 2.0 and 5.0. This value may be increased through repetitive use of the soap on a daily basis so that a cumulative effect is achieved.

BRIEF DESCRIPTION OF THE DRAWINGS

The present invention will be more fully understood by reference to the following detailed description of the preferred embodiments of the present invention when read in conjunction with the accompanying drawings, in which like reference characters refer to like parts throughout the views, and in which:

FIG. 2 is a micrograph similar to that shown in FIG. 1 but illustrating enhanced skin penetration of the sunscreen agent into the stratum corneum.

DETAILED DESCRIPTION OF THE PREFERRED EMBODIMENTS

A. Introduction

Figure 1:
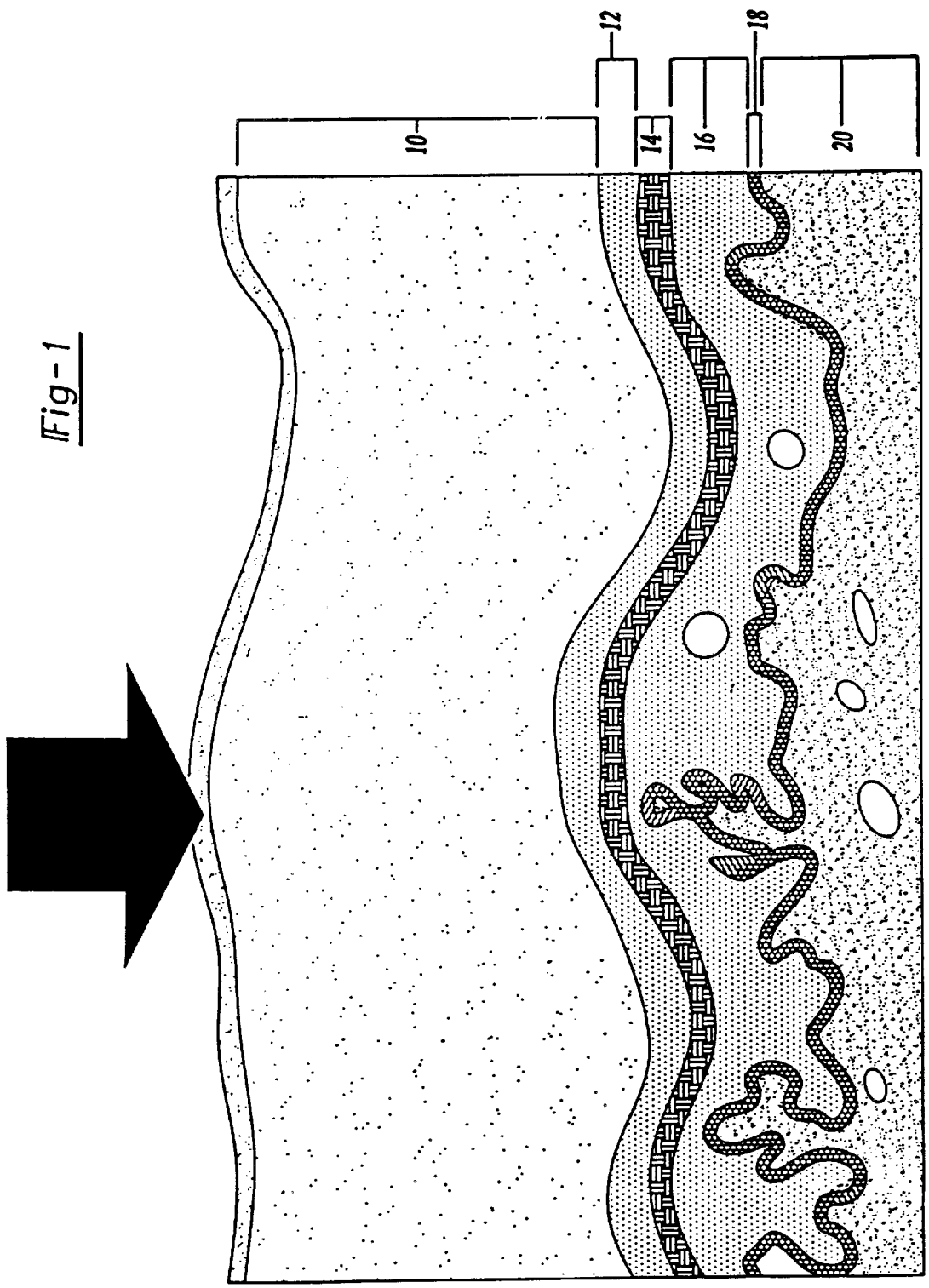
FIG. 1 is a micrograph of a section of human skin demonstrating minimal penetration of the stratum corneum by conventional sunscreen compositions.

The present invention relates to the topical use of compositions containing a cleansing component and a sunscreen component, both provided in safe and effective amounts, to provide protection against ultraviolet radiation including UVA and UVB. Preferred components include skin penetration enhancers and emollients, also provided in safe and effective amounts. The sunscreen composition may include a sunscreen component consisting of an organic sunscreen agent, an inorganic sunscreen agent, or both. The composition of the present invention achieves its preferred SPF value during washing and substantially maintains the SPF value even after hours of wear, thus amounting to a high degree of longevity and substantivity.

B. Sunscreen Components

As noted above, there are generally recognized two types of sunscreen mechanisms: Chemical absorption or physical blocking. Chemical or organic sunscreens typically include one or more ultraviolet B-absorbing chemical components, including generally organic compounds. As an alternative to the chemical sunscreen, so-called physical sunscreens are known and comprise generally inorganic particulate materials. These products utilize particles of zinc oxide or titanium dioxide suspended in a carrier for topical application.

Preferred among the sunscreen agents in general are any one or more of those agents selected from the group consisting of: 2-ethylhexyl p-methoxycinnamate, octyl salicylate, octocrylene, oxybenzone, 2-ethylhexyl N,N-dimethylaminobenzoate, p-aminobenzoic acid, 2-phenylbenzamidazole-5-sulfonic acid, homomenthyl salicylate, avobenzone (e.g., Parsol 1789), DEA p-methoxycinnamate, octylmethoxy cinnamate, 4/4'-methoxy-t-butyldibenzoylmethane, 4-isopropyldibenzoylmethane, 3-(4-methylbenzylidene) camphor, 3-benzylidene camphor, 4-N,N-dimethylaminobenzoic acid ester with 2,4-dihydroxybenzophenone, 4-N,N-dimethylaminobenzoic acid ester with 2-hydroxy-4-(2-hydroxyethoxy) benzophenone, 4-N,N-dimethylaminobenzoic acid ester with 4-hydroxydibenzoyl-methane, 4-N,N-dimethylaminobenzoic acid ester with 4-(2-hydroxyethoxy) dibenzoylmethane, 4-N,N-di(2-ethylhexyl)-aminobenzoic acid ester with 2,4-dihydroxybenzophenone, 4-N,N-di(2-ethylhexyl)aminobenzoic acid ester with 4-hydroxydibenzoylmethane, 4-N,N-di(2-ethylhexyl) aminobenzoic acid ester with 4-(2-hydroxyethoxy) dibenzoylmethane, 4-N,N-(2-ethylhexyl) methylaminobenzoic acid ester with 2,4-dihydroxybenzophenone, 4-N,N-(2-hydroxyethoxy) benzophenone, 4-N,N-(2-ethylhexyl)methylaminobenzoic acid ester with 4-hydroxydibenzoylmethane, 4-N,N-(2-ethylhexyl)methylaminobenzoic acid ester with 4-(2-hydroxyethoxy)dibenzoylmethane, titanium dioxide, iron oxide, zinc oxide, and mixtures thereof.

More preferred for use in the compositions described herein are the sunscreen agents selected from the group consisting of 2-ethylhexyl N,N-dimethyl-p-aminobenzoate, 2-ethylhexyl p-methoxycinnamate, octylmethoxy cinnamate, octocrylene, octyl salicylate, homomenthyl salicylate, p-aminobenzoic acid, oxybenzone, 2-phenylbenzamidazole-5-sulfonic acid, DEA p-methoxycinnamate, 4,4'-methoxy-t-butyldibenzoylmethane, 4-isopropyl dibenzoylmethane, 3-(4-methylbenzylidene) camphor, 3-benzylidene camphor, 4-N,N-(2-ethylhexyl)methylaminobenzoic acid ester with 4-(2-hydroxyethoxy)dibenzoylmethane, titanium dioxide, iron oxide, zinc oxide, and mixtures thereof.

Most (but not exclusively) preferred for use in the compositions described herein are the sunscreen agents selected from the group consisting of octylmethoxy cinnamate, oxybenzone, titanium dioxide, zinc oxide, and mixtures thereof.

The sunscreen agent according to the present invention can comprise from about 0.1% to about 25.0%, more preferably from about 1.0% to about 15.0%, and most preferably from about 5.0% to about 10.0% of the composition. The exact amounts and number of the selected sunscreen agent will vary depending upon the particular sunscreen agents selected and the preferred SPF factor.

One of the complaints against inorganic agents is the white coated appearance that they leave on the wearer. As an interesting variation to the conventional use of zinc oxides, some zinc-based compositions (e.g., Z-Cote® HP1

[registered trademark, SkinCeuticals]) provides micro-fine zinc oxide coated with a form of dimethicone. As expressed by the manufacturer, the dimethicone coating transforms the frequently granular and pasty particles of zinc oxide to a smooth formulation which is transparent. Other forms of micronized particles of inorganic blockers (such as micronized titanium dioxide) may also be useful in this regard. The micronizing of these particles achieves the important advantage of providing effective sunscreening without giving the appearance of skin coated with white paint.

In addition or alternatively, the sunscreen components may be encapsulated in microspheres or through other capsulization technology. This arrangement would provide the benefit of allowing time release of the sunscreen agent so as to provide longer-lasting protection to the wearer. Any application of microspheres, liposomes, nanoparticles, and nanoparticle technology for delivering a sunscreen agent to the skin may be incorporated to provide the time release effect.

Also to be noted in relation to inorganic blockers are Tioveil and Spectraveil (both of the Tioxide Group pic). Tioveil include products which are 40% dispersions of surface-treated titanium dioxide in a range of cosmetic vehicles. Spectraveil include products which are 60% dispersions of zinc oxide in a range of cosmetic vehicles. In certain variations, these products may be film-formers and may have advantageous uses here.

As a further variant of the use of chemical sunscreen agents, the present composition may employ an organic sunscreen such as octylmethoxy cinnamate trapped within a matrix. A commercial example of such a composition is found in SunCaps® (trademark, SkinCeuticals) in which the organic sunscreen molecules are evenly distributed throughout the particle. It is believed that use of trapped agents as part of a composition provide enhanced performance in the role of sunscreen.

It is important to note that any one of the preferred agents may be used individually as part of the composition or may be used in combination with other agents. It is also noteworthy that enhanced effects have been observed when one or more organic sunscreen agents are combined in a composition with one or more inorganic sunscreen agents.

C. Skin Penetration Enhancers

1. In General

The composition of the present invention may include one or more skin penetration enhancing agents. According to definition, "a chemical skin penetration enhancer increases skin permeability by reversibly damaging or by altering the physiochemical nature of the stratum corneum to reduce its diffusional resistance." (Abstract, *Skin Penetration Enhancers Cited in the Technical Literature*, D. W. Osborne and J. J. Henke [Research and Development, ViroTex Corporation, 4200 Research Forest Drive, Suite 350, The Woodlands, Tex. 77381], citing V. P. Shah, C. C. Peck, and R. L. Williams, *Skin Penetration Enhancement: Clinical Pharmacological and Regulatory Considerations* in Pharmaceutical Skin Penetration Enhancement, K. A. Walters and J. Hadgraft, Eds. [Dekker, New York, 1993.])

The agents for use in the present composition are to be provided in a safe and effective amount. By "safe and effective" it is meant an amount sufficient to enhance penetration of the sunscreen further into the skin than would be the case without use of such enhancers, but not so much as to cause any side effects or skin reactions in the composition, generally from about 1.0% to about 20.0% of the composition by weight.

Skin penetration enhancement may be graphically illustrated according to a comparison of FIGS. 1 and 2 which are micrographs of a section of human skin. This view in FIG. 1 illustrates the well-developed structural organization of an area such as the human hand. In this area, the epidermis is generally between 0.8 to 1.4 mm thick. (In other regions of the body, the epidermis may be much thinner, such as between 0.07 and 0.12 mm thick.)

The uppermost layer of the epidermis is the stratum corneum, generally labelled as 10. As is generally known, the fully keratinized cells of the stratum corneum are sloughed off over time, and are replenished by the production of replacement epidermal cells. The cells of the stratum corneum are not vascularized. Beneath the stratum corneum 10 are other layers of the epidermis, as defined by a stratum lucidum 12, a stratum granulosum 14, a stratum spinosum 16, and the lowermost level of the epidermis, a stratum germinativum 18 (stratum basale). Beneath the layers 10–18 which define the epidermis lies the dermis 20. The dermis 20 is highly vascularized. (As point of fact the stratum corneum 10 is occasionally referred to as the "stratum corneum proper" and, when combined with the stratum lucidum, is occasionally referred to collectively as the "stratum corneum." In a similar way, the stratum granulosum, the stratum spinosum, and the stratum basale are occasionally referred to as the "stratum malpighii.")

Ordinarily, when sunscreen lotions, creams, gels and the like are applied to the skin, their penetration into the skin is only nominal, as demonstrated by the arrow of FIG. 1. The shadowed area represents the depth of penetration theoretically achieved by known sunscreen compositions. This de minimis absorption results in only minimal protection to the user.

It might accordingly be preferred to provide means as part of a sunscreen composition whereby the sunscreen may penetrate the stratum corneum to a greater degree. Such penetration is demonstrated in FIG. 2. The arrow illustrates the sunscreen entering the skin and the shadowed area the approximate depth of ideal theoretical penetration. This composition would provide at least three advantages. First, by providing a skin penetration enhancement agent, the sunscreen would demonstrate more substantivity. By having penetrated further into the skin, the sunscreen would be less susceptible to removal by wearing or brushing off. Second, a more fully penetrated sunscreen would help in reducing free radical production, one of the undesirable biological by-products of exposure to the ultraviolet radiation of the sun. By having more complete presence in the stratum corneum, free radical production is minimized or is at least reduced. Third, for those free radicals which are produced, more complete penetration may allow for more effective free radical scavenging by therapeutic components such as antioxidants (e.g., butylated oxylated toluene (BHT), beta carotene, alphaglutathione and vitamins C and E).

Skin penetration enhancers are thought to work according to two mechanisms. One of these mechanisms is by improving the skin's reversible permeability to entry of materials having larger molecules which ordinarily would not enter the skin. The other mechanism relates to improved solubility of the selected active ingredient (in this instance, the sunscreen) in the stratum corneum. Of course, these two mechanisms—increased skin permeability and increased drug solubility—work together to improve skin penetration of an active agent.

2. Skin Penetration Enhancing Agents

Skin penetration enhancers present themselves in a variety of forms. Examples of skin penetration enhancers include the following: Ionic compounds (sodium pyrrolidone carboxylate [commonly known as "naturally moisturizing factor"], sodium hyaluronate, sodium lauryl sulfate [sodium dodecyl sulfate]), dimethyl sulfoxide and related compounds (cyclic sulfoxides, decylmethyl sulfoxide, 2-hydroxyundecyl methyl sulfoxide), Azone (Nelson Research) and its derivatives, solvents and related compounds (alkanols, diols, short-chain fatty acids, dimethyl acetamide, dimethyl formamide, ethanol/d-limonene combination, limonene, 3-phenyl-1-propanol, 3-phenyl-2-propen-1-ol, polyethylene glycol, polyoxyethylene sorbitan monoesters, polypropylene glycol, primary alcohols [tridecanol], propylene glycol, squalene, triacetin, trichloroethanol, trifluoroethanol, and trimethylene glycol).

Other skin penetration enhancers include: Fatty alcohols (aliphatic alcohols, decanol, lauryl alcohol [dodecanol], linolenyl alcohol, nerolidol, 1-nonanol, n-octanol, oleyl alcohol), fatty acid esters (diisopropyl sebacate), dodecyl N, N-dimethylamino acetate, dodecyl (N, N-dimethylamino)-butyrate, dodecyl N, N-dimethylamino isopropionate, dodecyl 2-(dimethylamino) propionate, ethyl acetate, glycerol monoethers, glycerol monolaurate, glycerol monooleate, glycerol monolinoleate, isopropyl myristate, isopropyl myristate/fatty acid monoglyceride combination, isopropyl myristate/ethanol/L-lactic acid combination, isopropyl palmitate, 1-monocaproyl glycerol, monoglycerides (medium chain length), oleyl oleate, sorbitan dilaurate, sorbitan dioleate, sorbitan monolaurate, sorbitan monooleates, sorbitan trilaurate, sorbitan trioleate, sucrose coconut fatty ester mixtures, sucrose monolaurate, sucrose monooleate), fatty acids (alkanoic acids, caric acids, diacid, ethylocyadecanoic acid, hexanoic acid, lactic acid, lauric acid, linoelaidic acid, linoleic acid, linolenic acid, neodecanoic acid, oleic acid, palmitic acid, pelargonic acid, propionic acid, vaccenic acid), fatty alcohol ethers (a-monoglyceryl ether, EO-2-oleyl ether, EO-5-oleyl ether, EO-10-oleyl ether, ether derivatives of polyglycerols and alcohols [1-0-dodecyl-3-0-methyl-2-00(29, 39-dihydroxypropyl) glycerol]).

Miscellaneous compounds and groups include: Various biologics (L-a-amino acids, lecithin, phospholipids, saponin/phospholipids, sodium deoxycholate, sodium taurocholate, sodium tauroglycocholate), enzymes (acid phosphatase, calonase, orgelase, papain, phospholipase-A-2, phospholipase-C, triacylglycerol hydrolase), miscellaneous amines and amides (e.g., urea), various complexing agents (beta- and gamma-cyclodextrin complexes, hydroxypropyl methylcellulose, liposomes, naphthalene diamide diimide, naphthalene diester diimide, macrocyclics, macrocyclic lactones, ketones, and anhydrides (optimum ring-16), unsaturated cyclic ureas, classical surfactants, various emulsifiers and wetting agents under the name Brij® (registered trademark, ICI Am. and ICI Spec. Chem.) including series 30, 36T, 35, 52, 56, 58, 72, 76, 78, 92, 96, and 98, cetyl trimethyl ammonium bromide, Empicol® ML26/F (registered trademark, Albright & Wilson, UK), HCO-60 surfactant, hydroxypolyethoxydodeeane, ionic surfactants (ROONa, ROSO3Na, RNH3Cl, R 5 8216), lauroyl sarcosine, nonionic surface active agents, nonoxynol, octoxynol, phenylsulfonate CA, Pluronic® F68, F127, and L62 (registered trademark, BASF), polyoleates (nonionic surfactants), Rewopal® HV10 (registered trademark, Rewo GmbH), sodium laurate, sodium lauryl sulfate (sodium dodecyl sulfate), sodium oleate, sorbitan dilaurate, sorbitan dioleate, sorbitan monolaurate, sorbitan monooleates, sorbitan trilaurate, sorbitan trioleate, Span® (registered trademark, ICI Spec. Chem.)(series 20, 40, and 85), Synperonic® NP (registered trademark, ICI Chem. & Polymers Ltd.), Triton® X-100 (registered trademark, Union Carbide), Tween™ (registered trademark, ICI Spec. Chem.) (series 20, 40, 60, 80, and 85).

In addition, there are a variety of miscellaneous enhancers which could be used as well. These include aliphatic thiols, alkyl N,N-dialkyl-substituted amino acetates, anise oil, biphasic group derivatives, bisabolol, cardamom oil, 1-carvone, ceramide sphingosine [and single lipids], chenopodium (70% ascaridol), chenopodium oil, cholesterol, cholesterol esters, 1,8 cineole (eucalyptol), cod liver oil (fatty acid extract), cyclodextrine, 4-decyloxazolidin-2-one, dicyclohexylmethylamine oxide, diethyl hexadecylphosphonate, diethyl hexadecylphosphoramidate, 4,4-dimethyl-2-undecyl-2-oxazoline, N-dodecanoyl-L-amino acid methyl esters, 1,3-dioxacycloalkanes (SEPAs), dithiothreitol, ethyl oleate, eucalyptol (cineole), eucalyptus oil, eugenol, herbal extracts, lactam N-acetic acid esters, N-hydroxyethalaceamide, 2-hydroxy-3-oleoyloxy-1-pyroglutamyloxypropane, menthol, methone, morpholine derivatives, N-oxide, nerolidol, octyl-b-D-(thio) glucopyranosides, various organic acids [salicylic acid, lactic acid, glycolic acid, citric acid], oxazolidinones, piperazine derivatives, polar lipids, polydimethylsiloxanes, polyacrylic acid and its polymers, poly[2-(methylsulfinyl) ethyl acrylate], polyrotaxanes, polyvinylbenzyldimethylalkylammonium chloride,poly(N-vinyl-N-methyl acetamide), prodrugs, saline (skin hydration), sodium pyroglutaminate, terpenes and azacyclo ring compounds, vitamin E (a-tocopherol), and ylang-ylang oil.

A separate individual group includes N-cyclohexyl-2-pyrrolidone, 1 -butyl-3-dodecyl-2-pyrrolidone, 1,3-dimethyl-2-imidazolikinone, 1,5 dimethyl-2-pyrrolidone, 4,4-dimethyl-2-undecyl-2-oxazoline, 1 -ethyl-2-pyrrolidone, 1 -hexyl-4-methyloxycarbonyl-2-pyrrolidone, 1-hexyl-2-pyrrolidone, 1-(2-hydroxyethyl)pyrrolidinone, 3-hydroxy-N-methyl-2-pyrrolidinone,1 -isopropyl-2-undecyl-2-imidazoline, 1-lauryl-4-methyloxycarbonyl-2-pyrrolidone, N-methyl-2-pyrrolidone, poly(N-vinylpyrrolidone), pyroglutamic acid esters, 2-pyrrolidone (2-pyrrolidinone).

In addition to the above, skin penetration enhancers suitable for use in the present composition may include mixtures of binary and trinary solvents. Such a mixture might include, for example, urea, glycerol and water.

While it is clear that a variety of skin penetration enhancers may find application in the present invention, two enhancers are of particular interest. It should be noted that these particular enhancers are set forth so as to be exemplary and not limiting.

The first of these, Transcutol® (registered trademark, Gattefosse Corporation), is diethylene glycol monoethyl ether. Transcutol® is a hygroscopic liquid, freely miscible with polar and non-polar solvents. Transcutol® is non-irritating and non-toxic. It is soluble in water, ethanol and oils. Transcutol® is thought to enhance drug flux across the stratum corneum by diffusion into this layer and by altering the solubility parameter of the agent itself. Data demonstrates that Transcutol® is able to increase drug flux without altering lag time, the implication being that Transcutol® works by altering the solubility of a permeant found in the skin. (Harrison et al., *The Relative Effect of Azone and*

*Transcutol on Permeant Diffusivity and Solubility in Human Stratum Corneum*, Pharmaceutical Research, Vol. 13, No. 4, 1996.)

Transcutol® is a good candidate for use as a binary vehicle with other components such as propylene glycol monolaurate (PGML), methyl laurate, or Labrafac Hydro (Gattefosse Corporation). An enhanced effect of such binary combinations has been observed and is supported by test results. Transcutol® has also demonstrated strong effectiveness when part of a ternary solvent system including Labrafac Hydro and a propylene glycol ester, D.P.P.G. (propylene glycol dipelargonate).

Another preferred skin penetration enhancer is a Velsan® formulation (e.g., Velsan® D8P-3 [isopropyl PPG-2-isodeceth-7 carboxylate; registered trademark, Sandoz)] and Velsan® DBP-16 [cetyl PPG-2 isodeceth-7 carboxylate]). Velsan® D8P-3 is particularly useful as a solvent.

It should be understood that the penetration enhancers according to the present invention assist to improve the wearability of the present composition. The enhancers improve adherence, adsorption and/or penetration of the sunscreen blocking agents (chemical or physical [i.e., organic or inorganic]) onto or into (or at least partially into) the stratum corneum. Whatever the mechanism brought about by the particular composition, the test evidence supports the value of utilizing skin penetration enhancers in several of the various combinations of the present invention.

D. Carriers

Preferred carriers for inclusion with the composition of the present invention include one or more surfactants. Surfactants or surface-active agents are provided as the primary cleaning component and are generally divided into three groups: detergents, wetting agents, and emulsifiers. As a practical matter, however, as all members of the group generally share the same chemical mechanism, no great effort will be made here to separate the preferred surfactants into separate groups.

Preferred surfactants/emulsifiers include any one of a great variety of nonionic, cationic, anionic, and zwitterionic emulsifiers. Reference may generally be made to McCutcheon's *Detergents and Emulsifiers*, North American Edition, 1986, incorporated herein by reference.

Generally, suitable surfactant/emulsifier types include esters of glycerin, esters of propylene glycol, fatty acid esters of polyethylene glycol, fatty acid esters of polypropylene glycol, esters of sorbitol, esters of sorbitan anhydrides, carboxylic acid copolymers (e.g., Pemulen® [TR-1 and TR-2][registered trademark, BF Goodrich]), alkyl methylmethacrylates (a member of the eudragid class), Gelucire® (registered trademark for saturated polyglycolized glyceride, Gattefosse SA), lecithins (specifically derived from soybean oil or egg yolk), esters and ethers of glucose, ethoxylated ethers, ethoxylated alcohols, alkyl phosphates, polyoxyethylene fatty ether phosphates, fatty acid amides, acyl lactylates, soaps and mixtures thereof. In addition, a desired amount of KOH (generally between 5.0 and 30.0 percent, preferably about 10.0 percent) may be incorporated as is known in general in the manufacture of soap and soap products.

One or more of the surfactants/emulsifiers of the present composition may include a carboxylic acid copolymer (an acrylic acid copolymer). These copolymers consist essentially of a colloidally water-soluble polymer of acrylic acid crosslinked with a polyalkenyl polyether of a polyhydric alcohol. Optionally, an acrylate ester or a polyfunctional vinylidene monomer may be included.

While many surfactants/emulsifiers are known, several types preferred for use in the present composition may, for illustrative purposes and without limitation, include the following: Sodium laureth sulfate, cocamidoprpyl betaine (amphosol), propylene glycol, glycerin, Span® 20, Tween® 20, sodium laureth sulfossucinate, stearyl alcohol, and such classic agents including various Brij® series (e.g., 30, 36T, 35, 52, 56, 58, 72, 76, 78, 92, 96, and 98), cetyl trimethyl ammonium bromide, Empicol® ML26/F, and HCO-60 surfactant.

The surfactants/emulsifiers may be used individually or as a mixture of two or more. Regardless of the number selected, the surfactants/emulsifiers preferably comprise from about 0.1% to about 40.0%, preferably from about 1.0% to about 20.0%, and most preferably from about 1.0% to about 10.0% of the compositions of the present invention.

In addition to the use of soaps, soapless cleansers may be used as well. For example, Oilatum® AD (registered trademark, Stiefel Laboratories), Aquanil™ (registered trademark, Person & Covey, Inc.), Cetaphil® (trademark, Galderma Laboratories, Inc.) or SpectroDerm® (registered trademark, Draxis Pharmaceutical Inc.) may be utilized as a soapless component in the present invention.

Furthermore, the composition of the present invention may be provided in a form which does not require water for rinsing. In such form, the user would simply apply the composition and wipe it off without the need for the use of water as a rinsing agent.

E. Water

The composition of the present invention comprises from about 5.0% to about 95.0%, more preferably from about 10.0% to about 80.0%, and most preferably from about 30.0% to about 60.0% of purified or deionized water. The exact level of water will depend upon the form (e.g., liquid soap or gel) of the product and the desired moisture content.

F. Additional Components

A wide variety of additional components may be selectively added to the composition of the present invention. The only caution is that the additional components be selected so as to avoid any undesirable reaction with the primary components (e.g., one or more of the sunscreen agents) of the composition. The *CTFA Cosmetic Ingredient Handbook*, Second Edition, 1992 (incorporated by reference herein), provides a broad source of possible cosmetic and pharmaceutical ingredients typically used in skin care compositions. Examples of such additional components include one or more of the following: Absorbents, abrasives, alphahydroxy acids, anti-acne agents, anticaking agents, antifoaming agents, antimicrobial agents (e.g., triclosan), antioxidants, binders, biological additives, buffering agents, bulking agents, chelating agents/sequestrants (e.g., disodium EDTA), chemical additives, colorants, cosmetic astringents, cosmetic biocides, denaturants, drug astringents, emollients (including glycerin alovera, and Vitamins A, C, and D [hydrating agents and skin protectants]), external analgesics, film forming copolymer (at a level of from about 0.1% to about 5.0%, preferably from about 0.1% to about 2.0%), foam boosters, fragrance components, gums, humectants/moisturizers (including urea, guanidine, glycolic acid, alphahydroxy acid, and glycolate salts, lactic acid and lactate salts, polyhydroxy alcohols such as sorbitol, glycerin, hexanetriol, propylene glycol, hexylene glycol and the like, polyethylene glycol, sugars and starches, sugar and starch derivatives, D-panthenol, hyaluronic acid, lactamide monoethanolamine, acetamide monoethanolamine, and mixtures thereof), hydrotropes, neutralizing agents, opacifying agents and pigments, pH adjusters, plasticizers, preservatives, propellants, reducing agents, skin bleaching agents, skin protectants, solubilizing agents, and suspending agents (e.g., Carbomer 1382).

Thickening agents or gellants may be added as desired to adjust the texture and viscosity of the composition. Such agents or gellants may be selected from Carbopol® resins [e.g., 934, 971, 974, 980, 981] and Pemulen(® [TR-1 and TR-2][both Carbopol ® and Pemulen® are registered trademarks of BF Goodrich], Noveon AA-1, ETD resins, and Ultrez® resins [registerd trademark, BF Goodrich]. In addition, carbomers might be useful for this purpose.

Optionally, various vitamins may be included in the composition of the present invention. Examples include Vitamin A and derivatives thereof (including, for example, retinol), ascorbic acid (Vitamin C and derivatives), Vitamin B, biotin, Vitamin D, Vitamin E and derivatives thereof such as tocopheryl acetate, betacarotene, panthothenic acid and mixtures thereof. In addition, a variant of Vitamin A, Retin-A (tretinoin, Ortho Pharmaceutical Corp.) may be incorporated into the present invention.

It may also be desired to include a non-polar wax component having a required HLB of from about 1 to about 8, more preferably from about 1 to about 7 and a melting point greater than about 50 degrees C., and preferably greater than about 60 degrees C. Examples of such useful waxes include ester waxes, diester waxes, hydrocarbon waxes, silicone waxes and triglyceride waxes and mixtures thereof.

G. Methods of Use

One of the many advantages of the composition of the present invention is that it is applied while washing. This characteristic facilitates ease of use and may have the added benefit of being cumulative. Accordingly, while demonstrating generally single-digit SPF values as a result of one-time use, repeated use (daily, for example) during ordinary washing is expected to increase SPF value over time.

The composition of the present invention is readily applied during washing in a suitable or effective amount and may be generally applied all over the body. A selected amount of the composition may be applied directly to the skin or may be used through intermediate application to a washcloth, pad, sponge, or other applicator. After lathering, dirt and sloughed-off skin may be washed away by rinsing with water leaving behind one or more of the sunscreen components. (When accompanied by one or more of the skin penetration enhancers listed above, the sunscreen penetrates the skin at least partially during the washing process.)

While it is ordinarily preferred to use the composition of the present invention in a manner similar to ordinary soap (i.e., wetting, application of composition, rinsing), it is also anticipated that the composition may be used by application without wetting followed by removal through, for example, wiping. This is the case for soapless cleansers described above.

H. Examples

The following non-limiting examples illustrate embodiments of the subject invention wherein both essential and optional ingredients are combined. It is to be understood that these examples are for illustrative purposes only and are not to be construed as limiting the scope of the invention thereto.

Ingredients are listed by weight percentage and are identified by chemical, CTFA, or trademarked names.

Various combinations have been tested for SPF results after 8 hours following application. These results successfully demonstrate the substantivity of the various compositions.

1. Organic Sunscreen-Based Compositions

Examples 1–15 disclose various organic sunscreen-based compositions. Sunscreen compositions disclosed in these examples were prepared by combining the following ingredients using conventional techniques.

EXAMPLES 1 THROUGH 15

| COMPONENT | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Sodium Laureth Sulfate | 10.00 | 10.00 | 10.00 | 20.00 | 20.00 | 20.00 | 20.00 | 20.00 | 10.00 | 10.00 | 10.00 | 10.00 | 10.00 | 10.00 | 10.00 |
| Cocamidopropyl Betaine | 5.00 | 5.00 | 5.00 | 10.00 | 10.00 | 10.00 | 10.00 | 10.00 | 5.00 | 5.00 | 5.00 | 5.00 | 5.00 | 5.00 | 5.00 |
| Transcutol | | 10.00 | 5.00 | | | | | | | | | | | | 10.00 |
| Octylmethoxy Cinnamate | 7.50 | 1.50 | 7.50 | 7.50 | 7.50 | 7.50 | 7.50 | 7.50 | 7.50 | 7.50 | 7.50 | 3.50 | 7.50 | 7.50 | 7.50 |
| Oxybenzone | 6.00 | 1.00 | 6.00 | | 6.00 | 6.00 | 6.00 | 6.00 | 6.00 | 6.00 | 6.00 | 3.00 | 6.00 | 6.00 | 6.00 |
| Propylene Glycol | | 1.00 | 1.00 | 1.00 | 1.00 | 1.00 | 1.00 | 1.00 | 1.00 | 1.00 | 1.00 | 1.00 | 1.00 | 1.00 | 1.00 |
| Span 20 | 2.40 | 2.40 | 2.40 | | | 2.40 | 2.40 | 2.40 | 2.40 | 2.40 | 2.40 | 2.40 | 2.40 | 2.40 | 2.40 |
| Tween 20 | 1.60 | 1.60 | 1.60 | | | 1.60 | 1.60 | 1.60 | 1.60 | 1.60 | 1.60 | 1.60 | 1.60 | 1.60 | 1.60 |
| Carbomer 1382 | 0.80 | 0.80 | 0.80 | 0.80 | 0.80 | 0.80 | 0.80 | 0.80 | 0.80 | 0.80 | 0.80 | 0.80 | 0.80 | 0.80 | 0.80 |
| Methylparaben | 0.10 | 0.10 | 0.10 | 0.10 | 0.10 | 0.10 | 0.10 | 0.10 | 0.10 | 0.10 | 0.10 | 0.10 | 0.10 | 0.10 | 0.10 |
| Disodium EDTA | 0.10 | 0.10 | 0.10 | 0.10 | 0.10 | 0.10 | 0.10 | 0.10 | 0.10 | 0.10 | 0.10 | 0.10 | 0.10 | 0.10 | 0.10 |
| 10% KOH | 5.00 | 5.00 | 5.00 | 5.00 | 5.00 | 5.00 | 5.00 | 5.00 | 5.00 | 5.00 | 5.00 | 5.00 | 5.00 | 5.00 | 5.00 |
| Sodium Laureth Sulfosuccinate | | | | | | | | | | | 12.00 | | | | |
| Isopropyl Myristate | | | | | | 2.00 | | | 2.00 | 2.00 | | | | | |
| Velsan D8P3 | | | | | | | 2.00 | | | | | 2.00 | 2.00 | 5.00 | 10.00 |
| Velsan D8P16 | | | | | | | | 2.00 | | | | | | | |
| Purified H$_2$O | 51.50 | 61.50 | 55.50 | 55.50 | 49.50 | 43.50 | 43.50 | 43.50 | 58.50 | 46.50 | 58.50 | 65.50 | 55.50 | 50.50 | 50.50 |
| Glycerin | 10.00 | | | | | | | | | | | | | | |
| FINAL SPF RESULTS: | | | | | | | | | | | | | | | |
| Subject 1 | 3.7 | 3.7 | 3.7 | 3.7 | 3.7 | 3.7 | 3.7 | 3.0 | 3.0 | 3.7 | 3.0 | 3.0 | 3.7 | 3.0 | 4.7 |
| Subject 2 | 3.0 | 3.0 | 3.0 | 3.0 | 3.0 | 3.0 | 3.7 | 3.0 | 3.8 | 3.0 | 3.8 | 3.0 | 4.7 | 3.8 | 3.7 |
| Subject 3 | 3.7 | 3.0 | 3.7 | 3.7 | 3.7 | 2.9 | 3.7 | 4.7 | 4.7 | 4.7 | 3.8 | 4.7 | 3.8 | 4.7 | 4.7 |
| Average | 3.47 | 3.23 | 3.47 | 3.47 | 3.47 | 3.20 | 3.70 | 3.57 | 3.83 | 3.80 | 3.53 | 3.57 | 4.7 | 3.83 | 4.37 |
| Standard Deviation | 0.40 | 0.40 | 0.94 | 0.40 | 0.40 | 0.44 | 0.00 | 0.98 | 0.85 | 0.85 | 0.46 | 0.98 | 0.55 | 0.85 | 0.58 |

With respect to Examples 1 through 3 and 6 through 15, the following technique was followed for creating the composition. The specified technique is preferred but is not exclusive.

Step 1: Measured amounts of the purified water, propylene glycol, and other water miscible excipients were placed in a suitable manufacturing vessel to create Part A in aqueous phase.

Step 2: The preservatives and chelating agents were dissolved in Part A to create Part B.

Step 3: The carbomer was dispersed into Part B to create Part C.

Step 4: A portion of the base was added to Part C to partially neutralize the composition to create Part D.

Step 5: The hydrophilic surfactants were added to Part D.

Step 6: Part E, the oil phase, was created through the combination of measured amounts of the surfactants, the sunscreens, and the oil emollients.

Step 7: Parts D and E were separately heated to about 80 degrees C.

Step 8: Part D was added to Part E to create Part F.

Step 9: Part F was run through a homogenizer.

Step 10: The homogenized Part F was cooled to a temperature below about 50 degrees C.

Step 11: The remainder of the base (10.0% KOH) was added to cooled Part F.

Step 12: Part F was thereafter repeatedly run through the homogenizer until a smooth/homogeneous composition was achieved.

With respect to Examples 4 and 5, the following technique is preferably although not exclusively followed for creating the composition.

Step 1: Measured amounts of the purified water, the preservatives, and the water miscible ingredients were placed in a suitable manufacturing vessel to create Part A.

Step 2: The carbomer was dispersed into Part A to create Part B.

Step 3: A portion of the base was added to Part B to partially neutralize the composition, resulting in Part C.

Step 4: While continuously mixing, hydrophilic surfactants and sunscreens were added to Part C to create Part D.

Step 5: The remainder of the base was added to Part D to create Part E.

Step 6: Continuous mixing of Part E was undertaken until a homogeneous system was achieved.

2. Inorganic Sunscreen-Based Compositions

Examples 16 through 24 disclose various inorganic sunscreen-based compositions. Sunscreen compositions disclosed in these examples were prepared by combining the following ingredients using conventional techniques.

EXAMPLES 16 THROUGH 24

| COMPONENT | 16 | 17 | 18 | 19 | 20 | 21 | 22 | 23 | 24 |
|---|---|---|---|---|---|---|---|---|---|
| Sodium Laureth Sulfate | 10.00 | 10.00 | 10.00 | 10.00 | 10.00 | 10.00 | 10.00 | 10.00 | 10.00 |
| Cocamidopropyl Betaine | 5.00 | 5.00 | 5.00 | 5.00 | 5.00 | 5.00 | 5.00 | 5.00 | 5.00 |
| Titanium Dioxide | 10.00 | 10.00 | | | 5.00 | 5.00 | 10.00 | 5.00 | 5.00 |
| Methylparaben | | | | 0.10 | 0.10 | | | 0.10 | 0.10 |
| Disodium EDTA | | | | 0.10 | 0.10 | | | 0.10 | 0.10 |
| Hydroxyethyl Cellulose | 0.80 | 0.80 | 0.80 | | | 0.80 | 0.80 | | |
| Glycerin | 30.00 | 30.00 | 30.00 | | | 30.00 | 30.00 | | |
| Silsoft 900 | 1.00 | 3.00 | | | | | | | |
| Sun Caps 664 | | | 25.00 | | | | | | |
| Cyclomethicone 345 | | | | 5.00 | | | | | |
| Z Cote HPI | | | | 5.00 | | | | | |
| White Petroleum | | | | 10.00 | | | | 10.00 | 10.00 |
| Stearyl Alcohol | | | | 2.00 | | | | 2.00 | 2.00 |
| BRIJ 72 | | | | 2.40 | | | | 2.40 | 2.40 |
| BRIJ 721 | | | | 1.60 | | | | 1.60 | 1.60 |
| Pemulen TR-2 | | | | 0.30 | | | | 0.30 | 0.30 |
| Cyclomethicone 345 | | | | | | | | 15.00 | 15.00 |
| 10% KOH | | | | 0.50 | | | | 0.30 | 0.30 |
| Propylene Glycol | | | | | 7.50 | | | | |
| 20% NaCl | | | | | 10.00 | | | | |
| Purified H$_2$O | 43.20 | 41.20 | 29.20 | 53.00 | 47.30 | 49.20 | 44.20 | 48.20 | 43.20 |
| Finsolv EMG-20 | | | | | | | | | 5.00 |
| FINAL SPF RESULTS: | | | | | | | | | |
| Subject 1 | 3.0 | 3.0 | 2.4 | 2.4 | 3.0 | 3.0 | 3.7 | 3.3 | 2.4 |
| Subject 2 | 3.8 | 3.8 | 3.8 | 2.4 | 2.4 | 3.0 | 3.7 | 3.0 | |
| Subject 3 | 3.7 | 3.0 | 3.0 | 2.4 | 3.0 | 3.0 | 3.8 | 3.8 | 3.0 |
| Average | 3.50 | 3.27 | 3.07 | 2.40 | 2.80 | 3.00 | 3.50 | 3.73 | 2.80 |
| Standard Deviation | 0.44 | 0.46 | 0.70 | 0.00 | 0.35 | 0.00 | 0.44 | 0.06 | 0.35 |

With respect to Examples 16 through 18 and 21 and 22, the following technique was followed for creating the composition. The specified technique is preferred but is not exclusive.

Step 1: Measured amounts of the glycerin and the titanium dioxide were placed in a suitable manufacturing vessel to create Part A.

Step 2: Part A was agitated using a stainless steel propeller mixer until a homogeneous mixture was achieved.

Step 3: The hydrophilic surfactants and enhancers were added to Part A to create Part B.

Step 4: Water was added to Part B to form Part C.

Step 5: The hydroxyethyl cellulose was dispersed in Part C through continuous mixing to form Part D.

Step 6: Part D was continuously mixed until a homogeneous system/gel was achieved.

With respect to Example 20, the following technique is preferably although not exclusively followed for creating the composition.

Step 1: Measured amounts of the purified water, the preservatives, and other water miscible ingredients were placed in a suitable manufacturing vessel to create Part A.

Step 2: A measured amount of titanium dioxide was added to Part A to create Part B.

Step 3: Part B was agitated using a stainless steel propeller mixer.

Step 4: Measured amounts of hydrophilic surfactants were added to Part B to create Part C.

Step 5: A measured amount of sodium chloride was added to Part C through continuous mixing.

Step 6: Part C was continuously mixed until a homogeneous system/gel was formed.

With respect to Examples 19, 23 and 24, the following technique was followed for creating the composition. The specified technique is preferred but is not exclusive.

Step 1: Measured amounts of the purified water, propylene glycol, and other water miscible excipients were placed in a suitable manufacturing vessel to create Part A in aqueous phase.

Step 2: The preservatives and chelating agents were dissolved in Part A to create Part B.

Step 3: The carbomer was dispersed into Part B to create Part C.

Step 4: A portion of the base was added to Part C to partially neutralize the composition to create Part D.

Step 5: The hydrophilic surfactants were added to Part D.

Step 6: Part E, the oil phase, was created through the combination of measured amounts of the surfactants, the sunscreens, and the oil emollients.

Step 7: Parts D and E were separately heated to about 80 degrees C.

Step 8: Part D was added to Part E to create Part F.

Step 9: Part F was run through a homogenizer.

Step 10: The homogenized Part F was cooled to a temperature below about 50 degrees C.

Step 11: The remainder of the base (10.0% KOH) was added to cooled Part F.

Step 12: Part F was thereafter repeatedly run through the homogenizer until a smooth/homogeneous composition was achieved.

3. Combination Organic/Inorganic Sunscreen-Based Compositions

Examples 25 through 31 disclose various organic/inorganic sunscreen-based compositions. Sunscreen compositions disclosed in these examples were prepared by combining the following ingredients using conventional techniques.

EXAMPLES 25 THROUGH 31

| COMPONENT | 25 | 26 | 27 | 28 | 29 | 30 | 31 |
|---|---|---|---|---|---|---|---|
| Octylmethoxy Cinnamate | 7.50 | 7.50 | 7.50 | 7.50 | 7.50 | 7.50 | 7.50 |
| Oxybenzone | 6.00 | 6.00 | 6.00 | | 6.00 | 6.00 | 6.00 |
| Titanium Dioxide (M212) | | | | | | | 10.00 |
| Tioveil IPM | | | 17.00 | 17.00 | | | |
| Tioveil TG | 17.00 | | | | | 17.00 | |
| Tioveil TGOP | | 17.00 | | | | | |
| Spectraveil IPM | | | | | 9.00 | | |
| Zinc Oxide (Z-Cote HPI) | | | | | | 5.00 | |
| Sodium Lauryl Ether Sulfate | 10.00 | 10.00 | 10.00 | 10.00 | 10.00 | 10.00 | 10.00 |
| Cocamidopropyl Betaine | 5.00 | 5.00 | 5.00 | 5.00 | 5.00 | 5.00 | 5.00 |
| Transcutol | | | 5.00 | 5.00 | 5.00 | 5.00 | |
| Methylparaben | 0.10 | 0.10 | 0.10 | 0.10 | 0.10 | 0.10 | |
| Disodium EDTA | 0.10 | 0.10 | 0.10 | 0.10 | 0.10 | 0.10 | |
| 10% KOH | 0.20 | 0.20 | 0.20 | 0.20 | 0.20 | 0.20 | |
| Hydroxyethyl Cellulose | | | | | | | 0.50 |
| Glycerin | 5.00 | 5.00 | | | | | 20.00 |
| Silsoft 900 | | | | | | | 1.00 |
| Brij 72 | 2.40 | 2.40 | 2.40 | 2.40 | 2.40 | 2.40 | |
| Brij 721 | 1.60 | 1.60 | 1.60 | 1.60 | 1.60 | 1.60 | |
| Pemulen TR2 | 0.10 | 0.10 | 0.10 | 0.10 | 0.10 | 0.10 | |
| Stearyl Alcohol | 2.00 | 2.00 | 2.00 | 2.00 | 2.00 | 2.00 | |
| White Petrolatum | 5.00 | 5.00 | 5.00 | 5.00 | 5.00 | 5.00 | |
| Purified Water | 38.00 | 38.00 | 38.00 | 44.00 | 46.00 | 33.00 | 40.00 |
| SPF RESULTS: | | | | | | | |
| Subject 1 | 3.0 | 3.0 | 3.0 | 2.4 | 3.0 | 4.7 | 4.7 |
| Subject 2 | 3.0 | 3.0 | 2.4 | 2.4 | 3.0 | 4.7 | 4.7 |
| Subject 3 | 3.0 | 3.0 | 3.0 | 2.4 | 3.0 | 4.7 | 4.7 |
| Average | 3.00 | 3.00 | 2.80 | 2.40 | 3.00 | 4.70 | 4.70 |

With respect to Examples 25 through 30, the following technique was followed for creating the composition. The specified technique is preferred but is not exclusive.

Step 1: Measured amounts of the purified water, propylene glycol, and other water miscible excipients were placed in a suitable manufacturing vessel to create Part A in aqueous phase.

Step 2: The preservatives and chelating agents were dissolved in Part A to create Part B.

Step 3: The carbomer was dispersed into Part B to create Part C.

Step 4: A portion of the base was added to Part C to partially neutralize the composition to create Part D.

Step 5: The hydrophilic surfactants were added to Part D.

Step 6: Part E, the oil phase, was created through the combination of measured amounts of the surfactants, the sunscreens, and the oil emollients.

Step 7: Parts D and E were separately heated to about 80 degrees C.

Step 8: Part D was added to Part E to create Part F.

Step 9: Part F was run through a homogenizer.

Step 10: The homogenized Part F was cooled to a temperature below about 50 degrees C.

Step 11: The remainder of the base (10.0% KOH) was added to cooled Part F.

Step 12: Part F was thereafter repeatedly run through the homogenizer until a smooth/homogeneous composition was achieved.

With respect to Example 31, the following technique was followed for creating the composition. The specified technique is preferred but is not exclusive.

Step 1: Measured amounts of the glycerin and the titanium dioxide were placed in a suitable manufacturing vessel to create Part A.

Step 2: Part A was agitated using a stainless steel propeller mixer until a homogeneous mixture was achieved.

Step 3: The hydrophilic surfactants and enhancers were added to Part A to create Part B.

Step 4: Water was added to Part B to form Part C.

Step 5: The hydroxyethyl cellulose was dispersed in Part C through continuous mixing to form Part D.

Step 6: Part D was continuously mixed until a homogeneous system/gel was achieved.

4. Time Delayed SPF Results—Examples 13, 15, and 22

In addition to testing for SPF substantially immediately following application of the various compositions as set forth above in Examples 1 through 31, additional testing was undertaken on Examples 13, 15, and 22 substantially eight hours after application. These results are set forth below and demonstrate the substantivity of select formulations of the present composition.

| TIME DELAYED SPF RESULTS | |
|---|---|
| Composition | SPF Results - Irradiated 8 Hours After Application |
| Example 13 | Subject 1 - 3.0 |
| | Subject 2 - 4.7 |
| | Subject 3 - 3.0 |
| | Average: 3.57 |
| | Standard Deviation - 0.98 |
| Example 15 | Subject 1 - 3.7 |
| | Subject 2 - 3.0 |
| | Subject 3 - 4.7 |
| | Average: 3.80 |
| | Standard Deviation - 0.85 |
| Example 22 | Subject 1 - 1.9 |
| | Subject 2 - 3.0 |
| | Subject 3 - 3.8 |
| | Average: <2.90 |
| | Standard Deviation: <0.95 |

5. Multiple Applications—Examples 13, 15, and 30

Testing was also done following repeated applications of select formulations of the present invention. As set forth below, at least one formulation of the present invention demonstrated a markedly improved SPF value following repeated applications. After the formulation of Example 30 was initially applied to certain subjects (e.g., Subject 7), repeated application/rinse on subsequent days over a period of five days more than tripled the SPF values of the formulation, demonstrating beneficial cumulative effects of repeated usage.

Testing was originally done only for Subject Nos. 4, 5, and 6. However, the tests performed on Subject Nos. 4, 5, and 6 were not intended to identify SPF values over 4.7. Accordingly, the tests were repeated for Subjects 7, 8, and 9.

| MULTIPLE APPLICATIONS | | |
|---|---|---|
| Composition | SPF Results - Day One (Initial Application) | SPF Results - Day Five |
| Example 13 | Subject 4 - 3.0 | Subject 4 - 3.0 |
| | Subject 5 - 4.7 | Subject 5 - <1.9 |
| | Subject 6 - 2.4 | Subject 6 - 2.4 |
| | Average: 3.37 | Average: <2.43 |
| Example 15 | Subject 4 - 3.0 | Subject 4 - 3.7 |
| | Subject 5 - 4.7 | Subject 5 - <1.9 |
| | Subject 6 - 2.4 | Subject 6 - 2.4 |
| | Average: 3.37 | Average: <2.67 |
| Example 30 | Subject 4 - 4.7 | Subject 4 - >4.7* |
| | Subject 5 - 2.4 | Subject 5 - 4.7 |
| | Subject 6 - 4.7 | Subject 6 - >4.7* |
| | Average: 3.93 | Average: >4.70 |
| Example 30 | Subject 7 - 3.7 | Subject 7 - 12.5 |
| | Subject 8 - >4.7* | Subject 8 - 12.5 |
| | Subject 9 - >4.7* | Subject 9 - 10.0 |
| | Average: >4.37 | Average: 11.67 |

*Testing was not done to identify SPF results over 4.7 in this instance.

6. Triethanolamine (TEA) Based Sunscreen Composition

Example 32 discloses a TEA based sunscreen composition according to a further variation of the present invention.

EXAMPLE 32

| | |
|---|---|
| Hard Paraffin | 25.0 |
| Soft Paraffin | 11.75 |
| Liquid Paraffin | 3.50 |
| Cetostearyl Alcohol | 5.00 |
| Triethanolamine | 0.70 |
| Stearic Acid | 0.20 |
| Sunscreen | As needed |
| QS DI Water | 100.00 |

The composition of Example 32 was prepared by melting the stearic acid with the oil being emulsified. The TEA was mixed with the water component and was warmed to the same temperature as the oily mixture. The oily emulsion was then added to the aqueous solution with constant but gentle stirring. This procedure was continued until the emulsion was cold. Vigorous stirring was avoided to reduce frothing.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

What we claim is:

1. A composition for use as a sunscreen for application during washing to the skin of a wearer, the composition comprising;

a soap component for cleansing the wearer's skin:

at least two photoprotective agents in a total amount of between about 0.1% and 25.0% by weight, said at least two photoprotective agents including at least one organic photoprotective agent and at least one inorganic photoprotective agent, said at least one inorganic photoprotective agent being selected from the group consisting of titanium dioxide and zinc oxide, at least one of said at least two photoprotective agents being encapsulated in a time-release capsule;

a carrier in an amount of between about 0.1% and 40.0% by weight;

a longevity and substantivity enhancing agent in an amount of between about 0.1% and 20.0% by weight, said longevity and substantivity enhancing agent being selected from the group consisting of ethoxyldiglycol and a carboxylate-based emollient; and water in an amount of between about 5.0% and 95.0%, whereby said encapsulation of said at least one of said at least two photoprotective agents provides time released delivery of said encapsulated photoprotective agent to the wearer's skin.

2. The composition for use as a sunscreen according to claim 1, wherein said at least one organic photoprotective agent is taken from the group consisting of octylmethoxy cinnamate and oxybenzone.

3. The composition for use as a sunscreen according to claim 1, wherein said at least two photoprotective agents are provided in an amount of between about 1.0% and 15.0% by weight.

4. The composition for use as a sunscreen according to claim 1, wherein said at least two photoprotective agents are provided in an amount of between about 5.0% and 10.0% by weight.

5. The composition for use as a sunscreen according to claim 1, wherein said soap component is provided in an amount of between about 1.0% and 20.0% by weight.

6. The composition for use as a sunscreen according to claim 1, wherein said soap component is provided in an amount of between about 5.0% and 10.0% by weight.

7. The composition for use as a sunscreen according to claim 1, wherein said soap component comprises one or more surfactants taken from the group consisting of detergents, wetting agents, and emulsifiers.

8. The composition for use as a sunscreen according to claim 1, wherein said soap component is a soapless cleanser.

9. The composition for use as a sunscreen according to claim 1, further including glycerin.

10. The composition for use as a sunscreen according to claim 1, wherein said at least one inorganic photoprotective agent is composed of micronized particles.

11. A composition for use as a sunscreen for application during washing, the composition comprising:

a sunscreen agent in an amount of between about 0.1% and 25.0% by weight, said sunscreen agent comprising at least two photoprotective agents, said at least two photoprotective agents including at least one organic photoprotective agent and at least one inorganic photoprotective agent, at least one of said at least two photoprotective agents being encapsulated in a time-release capsule;

a soap component in an amount of between about 0.1% and 40.0% by weight;

a longevity and substantivity enhancing agent in an amount of between about 0.1% and 20.0% by weight, said longevity and substantivity enhancing agent being a skin penetration enhancer, said skin penetration enhancer being selected from the group consisting of ethoxyldiglycol and a carboxylate-based emollient; and water in an amount of between about 5.0% and 95.0%, whereby said encapsulation of said at least one of said at least two photoprotective agents provides time released delivery of said encapsulated photoprotective agent to the wearer's skin.

12. The composition for use as a sunscreen according to claim 11, wherein said photoprotective agent is primarily an energy blocking agent.

13. The composition for use as a sunscreen according to claim 12, wherein said energy blocking agent is selected from the group consisting of titanium dioxide and zinc oxide.

14. The composition for use as a sunscreen according to claim 11, wherein said photoprotective agent is primarily an energy absorbing agent.

15. The composition for use as a sunscreen according to claim 14, wherein said energy absorbing agent is selected from the group consisting of octylmethoxy cinnamate and oxybenzone.

16. The composition for use as a sunscreen according to claim 11, wherein said longevity and substantivity enhancing agent is a skin penetration enhancer.

17. A composition for use as a sunscreen for application during washing, the composition comprising:

a paraffin;

cetastearyl alcohol;

an acid;

a photoprotective agent encapsulated in a time-release capsule; and water.

18. A composition for use as a sunscreen for application during washing to the skin of a wearer, the composition comprising:

a soap component for cleansing the wearer's skin;

at least two photoprotective agents, said at least two photoprotective agents including at least one organic photoprotective agent and at least one inorganic photoprotective agent, at least one of said at least two photoprotective agents being encapsulated in a time-release capsule;

a carrier in an amount of between about 0.1% and 40.0% by weight;

a longevity and substantivity enhancing agent in an amount of between 0.1% and 20.0% by weight, said longevity and substantivity enhancing agent being a skin penetration enhancer; and water in an amount of between about 5.0% and 95.0% by weight.

19. The composition for use as a sunscreen according to claim 18, wherein said at least two photoprotective agents total between about 0.1% and 25.0% by weight.

20. The composition for use as a sunscreen according to claim 19, wherein said at least one inorganic photoprotective agent is selected from the group consisting of titanium dioxide and zinc oxide.

21. The composition for use as a sunscreen according to claim 18, wherein said longevity and substantivity enhancing agent is a skin penetration enhancer.

22. The composition for use as a sunscreen according to claim 18, wherein said at least one organic photoprotective agent is taken from the group consisting of octylmethoxy cinnamate and oxybenzone.

23. The composition for use as a sunscreen according to claim 18, wherein said at least two photoprotective agents are provided in an amount of between about 1.0% and 15.0% by weight.

24. The composition for use as a sunscreen according to claim 18, wherein said at least two photoprotective agents are provided in an amount of between about 5.0% and 10.0% by weight.

25. The composition for use as a sunscreen according to claim 18, wherein said soap component is provided in an amount of between about 1.0% and 20.0% by weight.

26. The composition for use as a sunscreen according to claim 18, wherein said soap component is provided in an amount of between about 5.0% and 10.0% by weight.

27. The composition for use as a sunscreen according to claim 18, further including a film-forming agent.

28. The composition for use as a sunscreen according to claim 18, wherein said soap component comprises one or more surfactants taken from the group consisting of detergents, wetting agents, and emulsifiers.

29. The composition for use as a sunscreen according to claim 18, wherein said soap component is a soapless cleanser.

30. The composition for use as a sunscreen according to claim 18, further including glycerin.

31. The composition for use as a sunscreen according to claim 18, wherein said at least one inorganic photoprotective agent is composed of micronized particles.

32. The composition for use as a sunscreen according to claim 18, further including a paraffin.

33. The composition for use as a sunscreen according to claim 18, further including cetastearyl alcohol.

34. The composition for use as a sunscreen according to claim 18, further including triethanolamine.

35. The composition for use as a sunscreen according to claim 18, further including an acid.

36. A composition for use as a sunscreen for application to the skin during washing of the skin, the composition comprising:

at least two photoprotective agents in a total amount of between about 0.1% and 25.0% by weight, said at least two photoprotective agents including at least one organic photoprotective agent and at least one inorganic photoprotective agent, said at least one inorganic photoprotective agent being selected from the group consisting of titanium dioxide and zinc oxides, at least one of said at least two photoprotective agents being microencapsulated;

a carrier in an amount of between about 0.1% and 40.0% by weight;

a soap component which provides akin cleansing and skin penetrating effects, said soap component being a mixture of at least monoethanolamine, diethanolamine, and triethanolamine; and water in an amount of between 5.0% and 95.0%.

* * * * *

UNITED STATES PATENT AND TRADEMARK OFFICE
CERTIFICATE OF CORRECTION

PATENT NO. : 6,217,852 B1
DATED : April 17, 2001
INVENTOR(S) : Stuart R. Gildenberg et al.

It is certified that error appears in the above-identified patent and that said Letters Patent is hereby corrected as shown below:

Column 3,
Line 31, After "used" insert -- as --;

Column 7,
Line 21, "pic" should be -- plc --;

Column 9,
Line 61, "hydroxypolyethoxydodeeane" should be -- hydroxypolyethoxydodecane --;

Column 10,
Line 7, "Tween™" should be -- Tween® --;
Line 31, "chloride,poly" should be -- chloride, poly --;

Column 11,
Line 16, "DBP-16" should be -- D8P-16 --;

Column 13,
Table, Line 14, "Sulfosuccinate" should be -- Sulfossucinate --;
Table, Line 23, "4.7" should be -- 4.07 --;

Column 16,
Table, Line 2, Under Component 19 (Sodium Laureth Sulfate) "10.00" should be -- 15.00 --;
Table, Line 2, Under Component 20 (Sodium Laureth Sulfate) "10.00" should be -- 20.00 --;
Table, Line 3, Under Component 20 (Cocamidoprophy Betaine) "5.00" should be -- 10.00 --;
Table, Line 25, Under Component 23 (Subject 1), "3.3" should be -- 3.7 --;

Column 20,
Line 61, Amendment dated 11/8/99, ":" should be -- ; --;

UNITED STATES PATENT AND TRADEMARK OFFICE
CERTIFICATE OF CORRECTION

PATENT NO.   : 6,217,852 B1
DATED        : April 17, 2001
INVENTOR(S)  : Stuart R. Gildenberg et al.

It is certified that error appears in the above-identified patent and that said Letters Patent is hereby corrected as shown below:

Column 24,
Line 20, Amendment dated 11/8/99, "akin" should be -- skin --.

Signed and Sealed this

Eighth Day of February, 2005

JON W. DUDAS
*Director of the United States Patent and Trademark Office*